(12) United States Patent
Williams, III et al.

(10) Patent No.: US 6,862,890 B2
(45) Date of Patent: Mar. 8, 2005

(54) PROCESS FOR PRODUCTION OF NANOPARTICLES AND MICROPARTICLES BY SPRAY FREEZING INTO LIQUID

(75) Inventors: Robert O. Williams, III, Austin, TX (US); Keith P. Johnston, Austin, TX (US); Timothy J. Young, Midland, MI (US); True L. Rogers, Austin, TX (US); Melisa K. Barron, Conroe, TX (US); Zhongshui Yu, Austin, TX (US); Jiahui Hu, Austin, TX (US)

(73) Assignee: Board of Regents, University of Texas System, Austin, TX (US)

( * ) Notice: Subject to any disclaimer, the term of this patent is extended or adjusted under 35 U.S.C. 154(b) by 0 days.

(21) Appl. No.: 10/062,648

(22) Filed: Jan. 30, 2002

(65) Prior Publication Data

US 2003/0041602 A1 Mar. 6, 2003

Related U.S. Application Data

(60) Provisional application No. 60/264,988, filed on Jan. 30, 2001.

(51) Int. Cl.[7] ............................. F25D 17/02; F25C 1/18; B29B 9/00
(52) U.S. Cl. ................. 62/64; 62/70; 264/13
(58) Field of Search ................. 62/64, 70, 78; 264/5, 13

(56) References Cited

U.S. PATENT DOCUMENTS

| | | | | |
|---|---|---|---|---|
| 1,393,383 A | * | 10/1921 | Linebarger | 264/13 |
| 2,751,762 A | * | 6/1956 | Colton | 62/67 |
| 3,484,946 A | | 12/1969 | Sauer | 34/5 |
| 3,653,222 A | * | 4/1972 | Dunn et al. | 62/74 |
| 3,672,182 A | * | 6/1972 | Stowasser et al. | 62/70 |
| 3,721,725 A | | 3/1973 | Briggs et al. | 364/6 |
| 3,928,566 A | * | 12/1975 | Briggs et al. | 424/94.3 |
| 4,077,227 A | * | 3/1978 | Larson | 62/74 |
| 4,323,478 A | | 4/1982 | Adams et al. | 252/408 |
| 4,470,202 A | * | 9/1984 | Buxton et al. | 34/284 |
| 4,704,873 A | * | 11/1987 | Imaike et al. | 62/78 |
| 4,848,094 A | * | 7/1989 | Davis et al. | 62/78 |
| 5,145,684 A | | 9/1992 | Liversidge et al. | 424/489 |
| 5,208,998 A | | 5/1993 | Oyler, Jr. | 34/5 |

FOREIGN PATENT DOCUMENTS

WO  90/13285  11/1990  ............ A61K/9/16

OTHER PUBLICATIONS

Heller, M. C. et al., "Protein Formulation and Lyophilization Cycle Design: Prevention of Damage Due to Freeze–Concentration Induced Phase Separation," *Biotechnology and Bioengineering*, vol. 63, No. 2, Apr. 20, 1999, pp. 166–174.

(List continued on next page.)

*Primary Examiner*—William C. Doerrler

(57) ABSTRACT

The present invention provides a system and a method for the production of microparticles and nanoparticles of materials that can be dissolved. The system and method of the present invention provide quicker freezing times, which in turn produces a more uniform distribution of particle sizes, smaller particles, particles with increased porosity and a more intimate mixing of the particle components. The system and method of the present invention also produce particles with greater surface area than conventional methods. One form of the present invention provides a method for the preparation of particles. An effective ingredient is mixed with water, one or more solvents, or a combination thereof, and the resulting mixture is sprayed through an insulating nozzle located at or below the level of a cryogenic liquid. The spray generates frozen particles.

14 Claims, 2 Drawing Sheets

OTHER PUBLICATIONS

Maa, Yuh–Fun et al., "Protein Inhalation Powders: Spray Drying vs Spray Freeze Drying," *Pharmaceutical Research*, vol. 16, No. 2, 1999, pp. 249–254.

Rogers, T. L. et al., "Solution–Based Particle Formation of Pharmaceutical Powders by Supercritical or Compressed Fluid $CO_2$ and Cryogenic Spray–Freezing Technologies," *Drug Development and Industrial Pharmacy*, vol. 27, No. 10, 2001, pp. 1003–1015.

S. Palakodaty and P. York, Phase Behavioral Effects on Particle Formation Processes Using Supercritical Fluids, *Pharm. Res.*, vol. 16, 1999, pps. 976–985.

R. A. Bodmeier et al., "Polymeric Materials Formed by Precipitation with a Compressed Fluid Antisolvent, " *AIChE Journal*, vol. 39, 1993, pps. 127–139.

R. A. Bodmeier et al., "Polymeric Microspheres Prepared by Spraying into Compressed Carbon Dioxide," *Pharm Res.*, vol. 12 1995, pps 1211–1217.

R. A. Rajewski et al., "Pharmaceutical Processing with Supercritical Carbon Dioxide," *Journal of Pharm. Sci.*, vol. 86, 1997, pps. 885–890.

K. P. Johnston et al., "Rapid Expansion From Supercritical to Aqueous Solution to Produce Submicron Suspensions of Water–Insoluble Drugs," *Biotechnol. Prog.*, vol. 16, 2000, pps. 402–407.

* cited by examiner

PROCESS FOR PRODUCTION OF NANOPARTICLES AND MICROPARTICLES BY SPRAY FREEZING INTO LIQUID

CROSS REFERENCE

This application claims the benefit of U.S. Provisional Application No. 60/264,988 filed Jan. 30, 2001.

BACKGROUND OF THE INVENTION

Small particle engineering enables an active pharmaceutical ingredient (API) to be incorporated into a formulation for targeted drug delivery. Powder micronization can also be used to increase the dissolution rates of poorly water-soluble drugs.

Micronization procedures can modify particle size, porosity and density, and the API may be mixed with pharmaceutical excipients using small particle technologies to maximize delivery to the desired target for drug administration.

Particle formation technologies may be classified as either mechanical micronization processes or solution-based phase separation processes. Mechanical micronization methods include milling techniques such as that cited in U.S. Pat. No. 5,145,684. However, friction generated during these milling processes may lead to either thermal or mechanical degradation of the API. Spray drying, another common method used to micronize drug substances, requires extremely high temperatures, on the order of 150° C., to remove the solvent from the drug following atomization. The elevated temperatures may accelerate degradation of the active ingredient.

Solution-based techniques require less particle handling and are often easier to scale up than conventional milling techniques. Reduced particle handling results in higher yields and simplifies cleaning and sterilization procedures. Furthermore, solution-based processes can be continuous or semi-continuous unlike milling, which is typically a batch process.

Solution-based particle formation techniques involve the use of conventional liquids, or compressed gases, near-critical liquids or supercritical fluids functioning either as solvents, antisolvents, or cryogenic media for ultra-rapid freezing. These techniques involve phase separation of solvent and API either by evaporation, rapid expansion, change in solvent composition or solidification by freezing. The spray configuration in many of these processes produces atomized droplets with high surface areas. Thus phase separation and rapid nucleation result in small primary particles or highly porous microparticles.

Several solution-based phase separation techniques utilizing compressed fluids have been developed. Such micronization techniques typically employ liquid or supercritical fluid carbon dioxide as solvents or antisolvent, and involve atomization of a solution into the carbon dioxide from the vapor space above the carbon dioxide. The active ingredient is either contained in the solution or in the carbon dioxide itself. Precipitation of the active ingredient results in amorphous or crystalline powders. Such precipitation techniques are commonly referred to as, for example, precipitation with a compressed antisolvent (PCA), precipitation by rapid expansion from supercritical solutions (RESS), rapid expansion from supercritical to aqueous solution (RESAS) and are described in S. Palakodaty and P. York, Phase behavioral effects on particle formation processes using supercritical fluids, Pharm. Res., V. 16, 976–985 (1999); D. J. Dixon, K. P. Johnston and R. A. Bodmeier, Polymeric materials formed by precipitation with a compressed fluid antisolvent, AIChE J., V. 39, 127–139 (1993); R. Bodmeier, J. Wang, D. J. Dixon, S. Mawson and K. P. Johnston, Polymeric microspheres prepared by spraying into compressed carbon dioxide, Pharm. Res., V. 12, 1211–1217 (1995); B. Subramaniam, R. A. Rajewski and K. Snavely, Pharmaceutical processing with supercritical carbon dioxide, J. Pharm. Sci., V. 86, 885–890 (1997); and T. J. Young, S. Mawson, K. P. Johnston, I. B. Henriksen, G. W. Pace and A. K. Mishra, Rapid expansion from supercritical to aqueous solution to produce submicron suspensions of water-insoluble drugs, Biotechnol. Prog., V. 16, 402–407 (2000).

The success of the above-identified techniques depends heavily on the efficiency of atomization of the solution into the carbon dioxide. A disadvantage of such techniques when used with proteins and peptides is that many organic solvents used to dissolve the API also denature proteins and peptides. Therefore, such techniques may not lead to biologically active micronized protein powders. Even modified processes, utilizing an aqueous solution of proteins or peptides include the challenge of the low solubility of water in $CO_2$, the need for large quantities of organic solvent, optimization of the mixing of multiple streams, and denaturation of the protein that can occur due to the exposure of the protein to the acidic $CO_2$ (pH 3).

Another problem with the above-identified techniques is that they often require elevated temperatures to produce homogeneous precipitates, which elevated temperatures may enhance degradation of thermally labile drugs. Another disadvantage is the low solubility of most organic solids in supercritical $CO_2$, since low drug loading into the supercritical $CO_2$ results in low production rates of powders.

To dry the particles resulting from the above-identified solution methods, techniques include spray-freeze drying processes described in U.S. Pat. Nos. 3,721,725 and 5,208,998, and M. Mumenthaler and H. Leuenberger, Atmospheric spray-freeze drying: a suitable alternative in freeze-drying technology, Int. J. Pharm., V. 72, 97–110 (1991). A disadvantage of the above identified spray freeze-drying processes is that proteins can be easily denatured during freezing due to phase separation of water and its soluble components followed by ice crystal growth. Even modified spray freeze drying processes utilize expensive halocarbon refrigerants or result in unsuitably large particles.

It would be an advantage in the art of particle engineering for the pharmaceutical industry to provide a process which results in the formation of small particles without the problems associated with the above-identified prior art.

SUMMARY OF THE INVENTION

In one aspect, the present invention is a system for preparing particles comprising a solution source comprising an effective ingredient; a vessel for holding a cryogenic liquid; and an insulating nozzle having an end and a tip, wherein the end of the insulating nozzle is connected to the solution source and the tip is placed at or below the level of the cryogenic liquid.

In a second aspect, the present invention is a method for spray freezing comprising: mixing an effective ingredient with a solution agent; spraying the effective ingredient-solution agent mixture through an insulating nozzle located at or below the level of a cryogenic liquid, wherein the spray generates frozen particles. The particles may then be collected. The solvent is removed using, for example, lyophilization, to yield solid particles.

In yet a third aspect, the present invention is a particle that contains an effective ingredient and that has a size range of 10 nm to 10 $\mu$m, surface area of 0.5 $m^2/g$ to 115 $m^2/g$ as measured by the BET method, and a contact angle against purified water of 5 to 70 degrees.

The present invention provides a system and method for the production of microparticles and nanoparticles of materials. The present invention provides quicker freezing times than those techniques described in the above-identified prior art, which in turn produces a more uniform distribution of particle sizes, smaller particles, particles with increased porosity and a more intimate mixing of the particle components. The system and method of the present invention also produces particles with greater surface area than conventional methods.

The present invention provides a new process for producing microparticles and nanoparticles of pharmaceuticals by spray freezing into liquids (SFL). The SFL technique may be used to produce small particles containing one or more chemical agent(s) with or without an excipient. An excipient may be chosen to modify the intended function of the agent, such as to provide improved flow, enhance bioavailability or control/delay release of, for example, a pharmaceutical drug substance. Using the present SFL invention, for example, poorly soluble agents have been made more water-soluble by controlling the particle size, degree of crystallinity and mixing with excipients. Furthermore, the particles produced using SFL have a more uniform morphology that can be manipulated to enhance delivery and bioavailability. For example, the SFL method produces microparticles and nanoparticles that are useful for deep lung drug delivery due to the combination of particle density, drug bioavailability and the low degradation found using the SFL method disclosed herein.

Because the insulating nozzle is inserted directly into the cryogenic fluid, the droplets begin to freeze as or immediately after they are being formed. The intense atomization of the droplets resulting from the shear generated by the flow through the nozzle and cryogenic liquid produces extremely small droplets. The small droplet size further contributes to rapid freezing. The rapid freezing generates large supersaturation and thus rapid nucleation rates of dissolved substances. The rapid nucleation and restricted growth after the fine droplets are frozen leads to small primary particles on the order of 10 nm to 10 micron after drying. It minimizes the time for phase separation between the drug and excipients. As a result, the drug and excipients are intimately mixed, and this leads to high dissolution rates in drug delivery. The particles are smaller than those produced by other types of spray freezing processes because of the smaller drop sizes and faster freezing. The resulting high surface area particles offer numerous advantages in drug delivery. The faster freezing can prevent the formation of ice crystals and instead produce glassy solids. Glassy solids can often produce less drug denaturation and drug degradation than ice crystals, especially for peptides and proteins.

Figure 1:
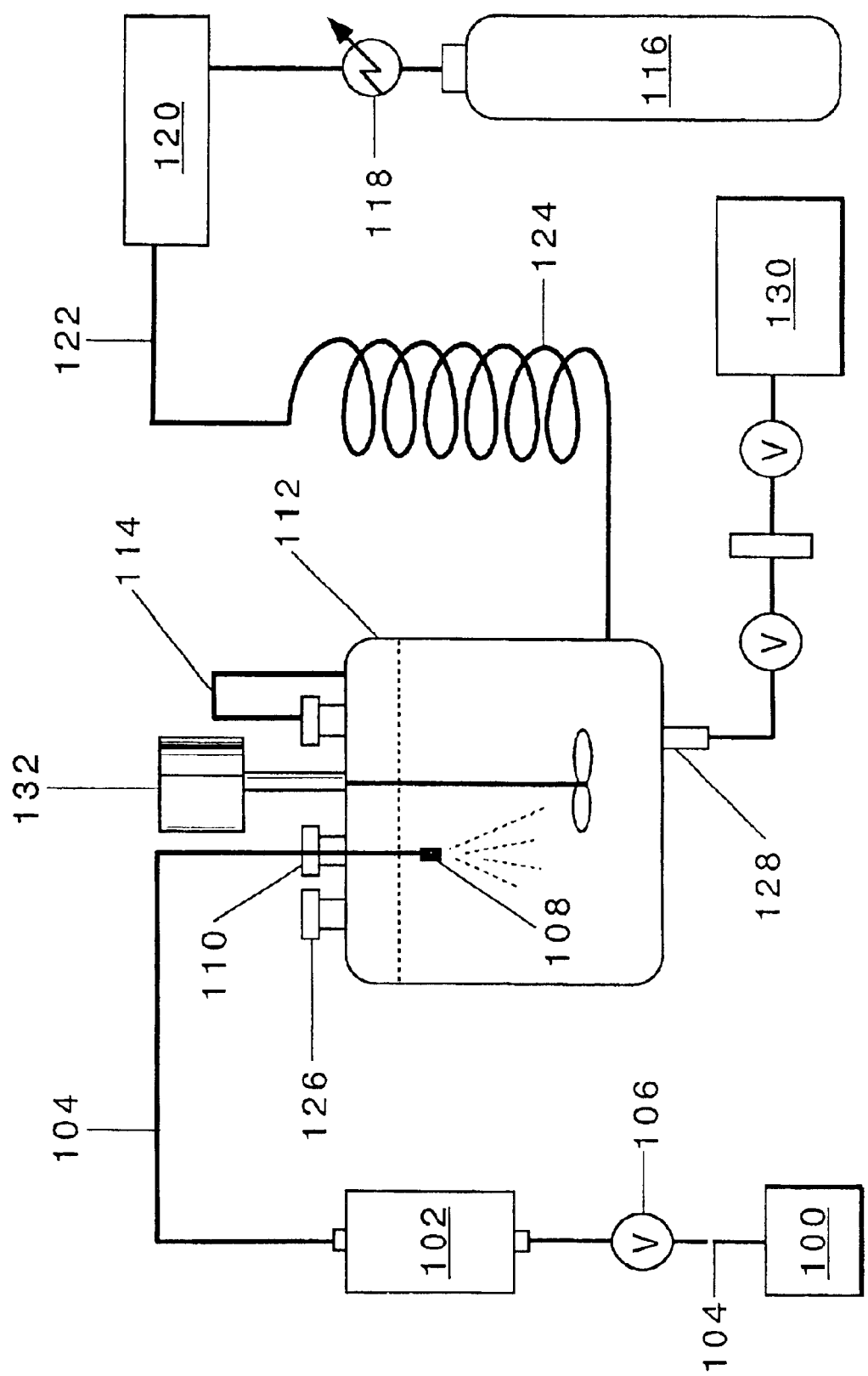
FIG. 1 depicts a schematic diagram of an apparatus for spray freezing into liquid in accordance with the present invention.

While the making and using of various embodiments of the present invention are discussed here in terms of an apparatus and method for producing microparticles and nanoparticles, it should be appreciated that the present invention provides many inventive concepts that can be embodied in a wide variety of specific contexts. The specific embodiments discussed herein are merely illustrative of specific ways to make and use the invention and are not meant to limit it in any way.

For the purposes of this application, the term "water soluble" is defined as requiring less than 1000 part water to dissolve 1 part solute. The term "poorly water soluble" is defined as requiring 1000 or more parts water to dissolve 1 part solute. The term "solution" as used in this application is meant to include suspensions and emulsions, as well as solutions.

The present invention provides a system and a method for producing extremely small particles, that is, microparticles and nanoparticles, by spray freezing a solution or suspension at the surface of or within a cryogenic liquid. The solution contains an effective ingredient and a solution agent, and can also contain any of a variety of adjuvants and/or excipients.

Non-limiting examples of effective ingredients are pharmaceuticals, peptides, nucleic acids, proteins, antibiotics, gene therapy agents, catalysts, adsorbents, pigments, coatings, personal care products, abrasives, particles for sensors, metals, alloys, ceramics, membrane materials, nutritional substances, anti-cancer agents, as well as, chemicals used in the agriculture industries such as fertilizers, pesticides and herbicides. It will be appreciated that this list is not exhaustive and is for demonstrative purposes only. It will be further appreciated that it is possible for one compound to be included in more than one class of effective ingredients, for example, peptides and pharmaceuticals.

Examples of pharmaceuticals include, but are not limited to, antibiotics, analgesics, anticonvulsants; antidiabetic agents, antifungal agents, antineoplastic agents, antiparkinsonian agents, antirheumatic agents, appetite suppressants, biological response modifiers, cardiovascular agents, central nervous system stimulants, contraceptive agents, diagnostic agents, dopamine receptor agonists, erectile dysfunction agents, fertility agents, gastrointestinal agents, hormones, immunomodulators, antihypercalcemia agents, mast cell stabilizers, muscle relaxants, nutritional agents, ophthalmic agents, osteoporosis agents, psychotherapeutic agents, parasympathomimetic agents, parasympatholytic agents, respiratory agents, sedative hypnotic agents, skin and mucous membrane agents, smoking cessation agents, steroids, sympatholytic agents, urinary tract agents, uterine relaxants, vaginal agents, vasodilator, anti-hypertensive, hyperthyroids, anti-hyperthyroids, anti-asthmatics and vertigo agents.

The pharmaceutical effective ingredients may be used in a variety of application modalities, including oral delivery as tablets, capsules or suspensions; pulmonary and nasal delivery; topical delivery as emulsions, ointments or creams; and parenteral delivery as suspensions, microemulsions or depot.

The solution agent used in the solution can be an aqueous such as water, one or more organic solvents, or a combination thereof. When used, the organic solvents can be water soluble or non-water soluble. Suitable organic solvents include but are not limited to ethanol., methanol, tetrahydrofuran, acetonitrile, acetone, tert-butyl alcohol, dimethyl sulfoxide, N,N-dimethyl formamide, diethyl ether, methylene chloride, ethyl acetate, isopropyl acetate, butyl acetate, propyl acetate, toluene, hexanes, heptane, pentane, and combinations thereof.

The excipients and adjuvants that may be used in the present invention, while potentially having some activity in their own right, for example, antioxidants, are generally defined for this application as compounds that enhance the efficiency and/or efficacy of the effective ingredients. It is also possible to have more than one effective ingredient in a given solution, so that the particles formed contain more than one effective ingredient.

As stated, excipients and adjuvants may be used to enhance the efficacy and efficiency of the effective ingredients. Non-limiting examples of compounds that can be included in the solutions that are to be spray frozen in accordance with the present invention include: surfactants, fillers, stabilizers, polymers, protease inhibitors, antioxidants and absorption enhancers. The excipients may be chosen to modify the intended function of the effective ingredient by improving flow, or bio-availability, or to control or delay the release of the effective ingredient. Specific nonlimiting examples include: Span 80, Tween 80, Brij 35, Brij 98, Pluronic, sucroester 7, sucroester 11, sucroester 15, sodium lauryl sulfate, oleic acid, laureth-9, laureth-8, lauric acid, vitamin E TPGS, Gelucire 50/13, Gelucire 53/10, Labrafil, dipalmitoyl phosphadityl choline, glycolic acid and salts, deoxycholic acid and salts, sodium fusidate, cyclodextrins, polyethylene glycols, labrasol, polyvinyl alcohols, polyvinyl pyrrolidones and tyloxapol. Using the process of the present invention, the morphology of the effective ingredients can be modified, resulting in highly porous microparticles and nanoparticles.

Any non-reactive cryogenic liquid is appropriate for use in the present invention. Cryogenic liquid is defined as any material (organic or inorganic) that remains liquid below the freezing point of water. Non-reactive is defined for the purposes of this application as not undergoing a chemical reaction with any of the components of the solution that is to be spray frozen. Non-limiting examples include: carbon dioxide, nitrogen, ethane, isopentane, propane, helium, halocarbons, liquid ammonia and argon. The cryogenic liquid can be held statically in a vessel, or can be circulated through an appropriate vessel that is equipped with a filter to collect the particles that are formed.

FIG. 1 diagrams one embodiment of an apparatus that can be used for the present invention. The effective ingredients and any excipients are dissolved and placed in the solution source 100 that is connected to a pump 102 via a delivery line 104 and a valve 106. The pump 102 may be an for example, HPLC pump, a syringe pump, or any other pump 102 capable of delivering the solution from the solution source 100 at the desired rate. The delivery line 104 may be stainless steel tubing or any other material suitable for use with a HPLC pump or a syringe pump.

The pump 102 is connected to an insulating nozzle 108 via delivery line 104. Located between solution source 100 and nozzle 108 may be a valve 110. For the purposes of this application, an "insulating nozzle" is any nozzle that does not become blocked when positioned at or within a cryogenic liquid while a solution is being passed through it, and that has no active defrosting apparatus connected to it. In one particular embodiment the insulating nozzle 108 tip is positioned substantially at the interface of the cryogenic liquid, thereby decreasing the amount of insulative property that the insulating nozzle 108 will require to prevent the solution that is traversing the insulating nozzle 108 from freezing. As will be apparent to those of skill in the art, in light of the present disclosure, the properties of the solution (pH, salt content, excipient, solubilizing agents, solvent) will affect the solutions ability to freeze. In addition to intrinsic factors or characteristics of the solution, the manner of application through the insulating nozzle 108 will affect freezing, for example, flow rate and pressure.

The insulating nozzle 108 has an end that is defined as the location where material to be spray freezed enters the insulating nozzle 108. The insulating nozzle 108, also has a tip, which is defined as the location where the material to be spray frozen exits the insulating nozzle 108. The insulating nozzle 108 is positioned such that the insulting nozzle tip is at or below the top surface of a cryogenic liquid in vessel 112.

The vessel 112 may be, for example, a sealed pressure vessel, as shown, for working with cryogenic liquids that liquefy at pressures above atmospheric, for example, carbon dioxide, or it may be an open top vessel for cryogenic liquids that are liquids at ambient pressures, for example, inorganic or organic molecules, such as nitrogen or ethanol, respectively. The vessel 112 will generally act as a static reservoir, but may permit continuous flow of the cryogenic liquid.

The insulting nozzle 108 may be composed of, for example, a molded tip. Molded tips for use with the invention may be made primarily of, for example, a polyetheretherketone such as PEEK. Another example is a molded tip made of polyether block amide such as PEBAX or a thermoplastic polyurethane elastomer such as PELLETHANE on tubing made of a polyetheretherketone. The insulating nozzle 108 may also be made of any non-reactive insulating material, for example, nylon, rayon, polyester, glass etc., and may even be coated with TEFLON or another material with a substantially low coefficient of friction. It may also be made of a metal with or without outer insulation. The inner diameter of the nozzle can range from one micron to one centimeter. The thickness of the insulating nozzle 108 ranges from 0.5 mm to 10 cm. The insulating nozzle 108 is generally attached to the delivery line 104 coming from the solution source 100 by a sealed tubing having a connection capable of withstanding operating pressures. However, any attachment method that can withstand the pressure within the line is appropriate.

Several other ports may be included in the vessel 112. One such port may serve as an inlet port for the cryogenic gas or liquid 114. The cryogenic liquid 114 can be pumped into the vessel 112 from a compressed gas tank 116 that is connected to a regulator 118 and a filter and drying unit 120.

The cryogenic liquid 114 passes through tubing 122 that passes through a chilled ethanol dry ice bath 124. Other ports that can be connected to the vessel include a release valve 126 and a pressure and temperature transducer port 128 that is connected to display equipment 130. A stirrer 132 can also be used in this version of the present invention.

In operation, the effective ingredient or ingredients are dissolved or suspended in a solution agent (organic, aqueous-organic or aqueous system) and placed in a solution source, for example, solution source 100. The ingredient and solvent may be pre-sterilized before particle formation. Likewise, the entire, sealed apparatus may be sterilized prior to use, thereby providing particles that may used directly or packaged in a sterile manner for future use. The solution source 100 may be made, for example, stainless steel and may contain one or more low- or high-pressure fittings.

The solution source 100 may itself act as a pump by adding a piston that drives the solution within the solution source into or toward the insulating nozzle 108. In one example, pressure within the solution source 100 may be increased by pressurized gas, for example, carbon dioxide. The delivery of the gas and the pressure in the solution source 100 may be controlled by, for example, a digital syringe, or even an HPLC pump. The choice of pump will be apparent to, and readily within, the skills of the artisan.

Table 1 contains examples of SFL conditions for the creation of microparticles and nanoparticles using the present invention.

TABLE 1

Microparticle Formation in $CO_2$

| Agent | Excipient | Temperature | Pressure | Nozzle | Liquid Flow Rate | Cryogen Flow rate |
|---|---|---|---|---|---|---|
| Albuterol sulfate, Triamcinolone Acetonide, Insulin | 10 percent PEG, 18,5000 MW | −40 C. | 1000 psig | 0.005" | 1–10 ml/min | 35 ml/min. |
| Albuterol sulfate, Triamcinolone Acetonide, Insulin | 10 percent PEG, 18,5000 MW | −40 C. | 1000 psig | 0.005" | 1–10 ml/min | 17.5 ml/min. |
| Albuterol sulfate, Triamcinolone Acetonide, Insulin | 10 percent PEG, 18,5000 MW | −40 C. | 1000 psig | 0.005" | 1–10 ml/min | 5 ml/min. |
| Albuterol sulfate, Triamcinolone Acetonide, Insulin | 10 percent PEG, 8,000 MW | −40 C. | 1000 psig | 0.005" | 1–10 ml/min | 2 ml/min. |
| Albuterol sulfate, Triamcinolone Acetonide, Insulin | 10 percent PEG, 8,000 MW | −40 C. | 1000 psig | 0.005" | 1–10 ml/min | 5 ml/min. |
| Albuterol sulfate, Triamcinolone Acetonide, Insulin | 2 percent PEG, 18,500 MW | −40 C. | 1000 psig | 0.005" | 1–10 ml/min | 2 ml/min. |
| Albuterol sulfate, Triamcinolone Acetonide, Insulin | 2 percent PEG, 18,5000 MW | −40 C. | 1000 psig | 0.0025" | 1–10 ml/min | 2–35 ml/min. |
| Albuterol sulfate, Triamcinolone Acetonide, Insulin | 10 percent PEG, 8,000 MW | −40 C. | 1000 psig | 0.005" | 1–10 ml/min | 2–35 ml/min. |

Figure 2:
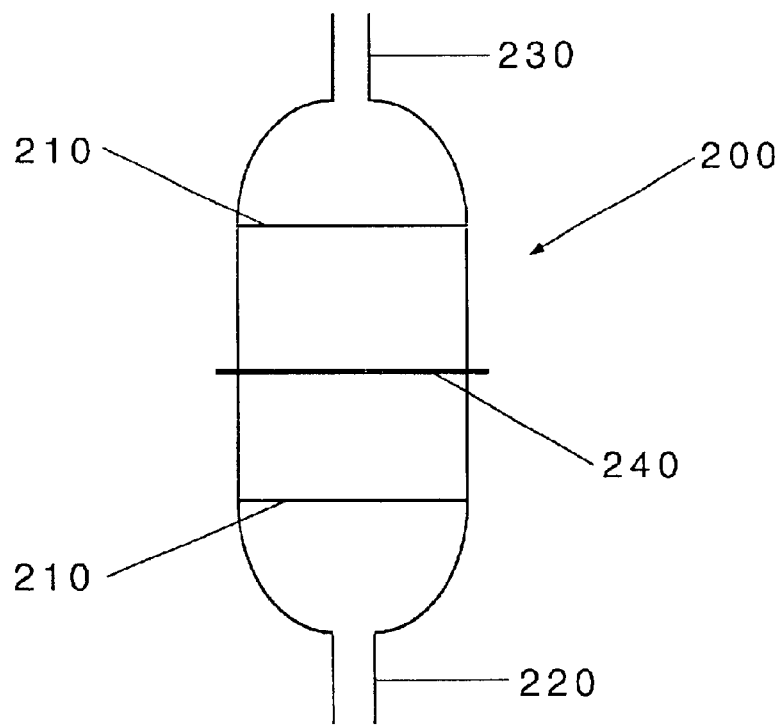
FIG. 2 depicts an apparatus for removing the solvent from the particles produced in accordance with the present invention.

A filter drying unit 200 is depicted in FIG. 2. The freeze-sprayed particles are transferred to the unit 200 so that they reside between two porous filter elements 210. The porous filter elements 210 can be of any material that allows retention of the particles within the unit 200. Examples of a suitable porous filter element 210 include a glass frit, a blown-through filter cloth, a screen, a porous disc, or other suitable porous filter elements, as well as other components which may be envisaged by those of skill in the art in light of the present disclosure.

The frozen particles are introduced into the unit 200 via an access joint 240. The unit 200 is attached to a source of cooled gas via inlet 220. The incoming gas will most often be cooled to a temperature below the melting point of the particles so that greatly reduced redissolution takes place. If necessary, the entire unit 200 can be cooled externally, by immersion in a suitable refrigerant. The cooled gas passes through the unit 200 from the bottom to top and passes out of the unit 200 via outlet 230. In this manner the solvent is removed from the frozen particles.

Figure 3:
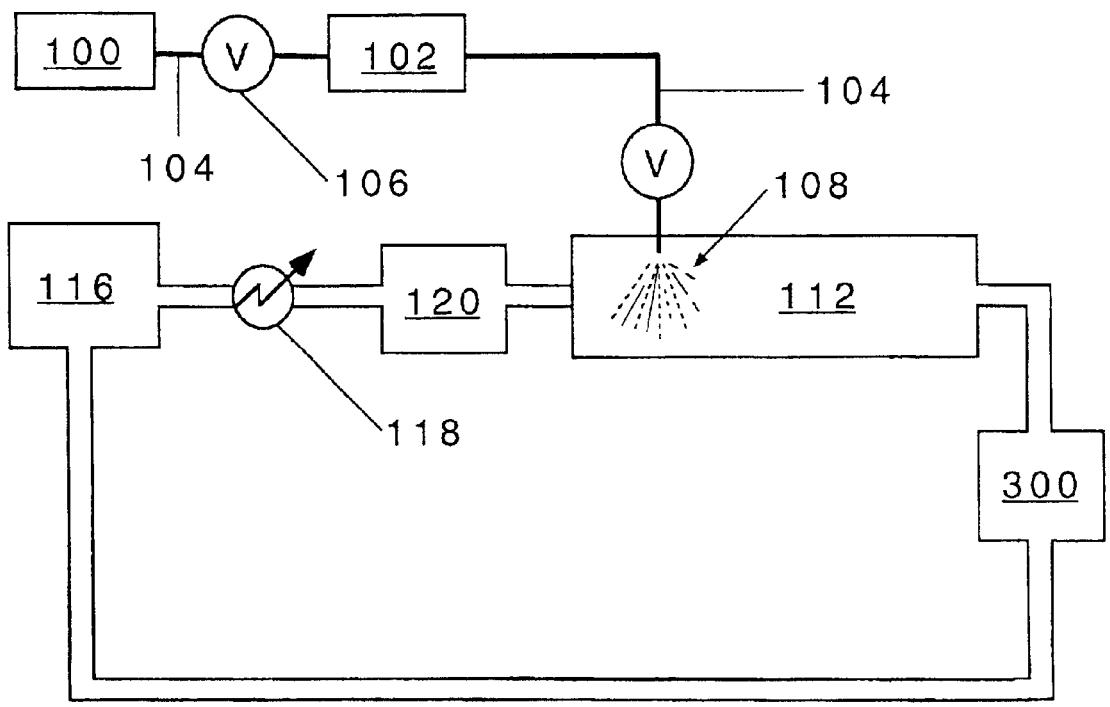
FIG. 3 depicts an apparatus capable of continuous flow operation in accordance with the present invention.

The process may also be operated in a continuous flow mode as depicted in FIG. 3. By using a continuous flow of the solution source 100 and/or the cryogenic liquid the throughput of the compound that is being spray frozen may be increased dramatically with the incorporation of a filtration unit 300 for the removal of the frozen particles. As will be known to those of skill in the art of pharmaceutical automation, it will be useful that the system is self-contained and capable of being sterilized. In this manner the spray freezing occurs in continuous mode and the microparticles or nanoparticles are captured downstream from the spray freezing site. The capture mechanism may include a bucket or conveyor belt system that takes the particles and places them in storage for subsequent processing or for removal of the solvent.

Whether using the batch or the continuous flow method, the size, shape, density, porosity and flowability of the particles may be modified by, for example, varying the solvent, and the relative proportion of any cosolvent (when one is used). It is also possible to alter the morphology of the particles by varying the temperature of the solution in the solution source, the concentration of the solutes, the flow rate of the solution through the nozzle, the inner diameter and/or shape of the nozzle and the pressure drop between the transfer line and the nozzle, to name a few options. Those of skill in the art will recognize that known parameters may be used, with minimal investigation, to obtain desired particle sizes.

The particles containing the active compound(s) may be administered with or without a propellant into, for example, the deep lung or even orally. When administered orally the particles may be provided with, for example, an inert diluent or with an assimilable edible carrier, or they may be enclosed in hard or soft shell gelatin capsule, or they may be compressed into tablets, or they may be incorporated directly with the food of the diet.

For oral therapeutic administration, the particles containing the active compound(s) may be incorporated with excipients and used in the form of ingestible tablets, buccal tablets, troches, capsules, elixirs, suspensions, syrups, wafers. Such compositions and preparations should contain at least 0.1 percent of active compound. The percentage of the compositions and preparations may, of course, be varied and may conveniently be between 2 to 60 percent of the weight of the unit. The amount of particles containing the active compound(s) in such therapeutically useful compositions is such that a suitable dosage will be obtained.

The present invention finds particular uses in the delivery of particles of low density and large size for drug delivery to the pulmonary system. Inhaled aerosols have been used for the treatment of local lung disorders including asthma and cystic fibrosis and have potential for the systemic delivery of peptides and proteins. The particles containing the active compound(s) of the present invention may be used with local and systemic inhalation therapies to provide controlled release of the therapeutic agent.

The particles containing the active compound(s) provided herein, permit for an effective dry-powder inhalation therapy for both short and long term release of therapeutics, either for local or systemic delivery, with minimum aggregation.

While not wishing to be bound by theory, the increased particle size consistency is expected to decrease the particles' clearance by the lung's natural mechanisms until drugs have been effectively delivered.

As used herein, "pharmaceutically acceptable carrier" includes any and all solvents, dispersion media, coatings, antibacterial and antifungal agents, isotonic and absorption delaying agents. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The particles containing the active compound(s) may be included in a transdermal device and may include, in its most basic embodiment, a reservoir adapted to retain during storage and release in operation the particles containing the active compound(s) produced using the present invention. It will be appreciated that a wide variety of transdermal devices have been described in the art and are suitable for use in the present invention.

EXAMPLES

The following terms are used in the subsequent examples.

"Danazol" is a poorly water soluble (aqueous solubility=0.17–0.22 μg/ml) glucocorticoid derivative that is used commercially in the treatment of breast cancer and endometriosis.

"THF" is tetrahydrofuran.

"HPβCD" is hydroxypropyl-β-cyclodextrin.

"SFL" means spray freezing into liquid and refers to the process of the present invention.

"XRD" means x-ray diffraction.

"Slowly frozen control" refers to a sample made by placing the drug solution on the tray of a lyophilizer and then slowly cooling the tray to freeze the sample. The ice is then sublimed.

"Co-ground physical mixture" refers to a sample prepared by admixing the active with the excipients in a ceramic mortar, then mixing with a pestle to provide intimate contact and particle size reduction of the powders.

"ATMFD" means atmospheric freeze-drying.

"FeSSIF" means fed state simulated intestinal fluid prepared by a recipe known in the art.

This media is used to simulate gastrointestinal conditions. FeSSIF is the dissolution media that the powders produced in the following examples are dispersed into to quantitate the amount of drug dissolved as a function of time.

"CBZ" refers to carbamazepine, a well-established drug used in the treatment of epilepsy, having an aqueous solubility of 61 μg/mL.

"SLS" refers to sodium lauryl sulfate.

"TAA" means triamcinolone acetonide, a long-acting synthetic glucorticoid, which is poorly water soluble (aqueous solubility=21 μg/mL.

"PVP K-15" means polyvinyl pyrrolidone with an approximate molecular weight of 8000.

"Poloxamer 407" means.polyoxyethylene-polyoxypropylene copolymer with an average molecular weight distribution of 9840 to 14600

"sCT" means salmon calcitonin.

Example 1

An aliquot of 0.1 g bovine insulin was dissolved in 20 ml HCl (pH=2), the solution was then titrated by 0.1 N NaOH to pH 7.4. The feed solution was then atomized using an ISCO pump by spray freezing into liquid nitrogen. The nozzle used was polyetheretherketone tubing with a diameter of 63.5 μm. The flow rate was 14 ml/min at 4000 psi. The frozen particles were collected and dried in a tray lyophilizer. The products were characterized by different techniques, and the results are shown in Table 2. The resulting particles were highly porous. The SFL process did not influence the chemical stability of insulin as indicated by no change in the level of A-21 desamido insulin (Table 2). The SFL process decreased the level of covalent insulin dimer (Table 2). The mean particle size diameter as determined by time-of-flight measurement was 5.06 microns. SEM photographs reveal that the particle is an aggregate composed of small domains of insulin.

TABLE 2

The physical and chemical characteristics of SFL insulin powder compared to bulk insulin powder.

| | A-21 desamido insulin (percent) | Covalent Insulin Dimer (percent) | BET surface area ($m^2$/g) | Mean Particle Size (μm) |
|---|---|---|---|---|
| SFL insulin powder | 3.04 | 0.36 | 30.16 | 5.06 |
| Bulk insulin | 3.03 | 0.25 | | 14.24 |

Example 2

The SFL insulin powder was prepared according to the procedure outlined in Example 1 with same formulation. The SFL insulin powder was stored at −4° C. The samples were taken out at 6, 12 and 24 weeks. SEM photographs showed that the particles were still porous after 24 weeks storage. The percentage of A-21 desamido and covalent insulin dimer in the sample are summarized in Tables 3 and 4.

TABLE 3

The percentage of A-21 desamido in the samples that was stored for different time periods.

| | Initial | 6 weeks | 12 weeks | 24 weeks |
|---|---|---|---|---|
| SFL insulin powder | 2.45 | 2.72 | 3.04 | 3.03 |
| Bulk insulin | 2.46 | | 2.61 | 2.72 |

TABLE 4

The percentage of covalent insulin dimer in the samples which were stored for different time periods.

| | Initial | 6 weeks | 12 weeks | 24 weeks |
|---|---|---|---|---|
| SFL insulin powder | 0.5 | 0.55 | 1.47 | 1.25 |
| Bulk insulin | 0.5 | | 1.18 | 1.15 |

Example 3

Aliquots of 50 mg sCT, 10 mg tyloxapol, and 250 mg lactose were dissolved in 40 ml of deionized water to make the SFL feed solution. Then the feed solution was pressurized using an ISCO syringe pump and atomized by spray freezing into liquid nitrogen. The nozzle used was polyetheretherketone tubing with inner diameter of 63.5 μm. The flow rate was 14 ml/min at a 4000 psi. The frozen particles were collected and dried in a tray lyophilizer. The physical properties are summarized in the Table 5.

TABLE 5

The physical characteristics of SFL calcitonin powder which was sprayed with tyloxapol and lactose.

| | BET surface area (m$^2$/g) | Mean Particle Diameter ($\mu$m) |
|---|---|---|
| SFL calcitonin powder | 19.16 | 10.49 |

Example 4

An aliquot of 0.085 g danazol was dissolved in 14.85 g THF, and 0.365 g HPβCD was dissolved in purified water. The two solutions were mixed and allowed to equilibrate to generate a water-soluble inclusion complex between danazol and HPβCD. The solution was then processed by SFL and freeze-dried in a tray lyophilizer. The solution was atomized directly into liquid nitrogen through an insulated polyetheretherketone (PEEK) nozzle with a 63.5 $\mu$m orifice at 5000 psi constant pressure supplied by an ISCO syringe pump. The atomized frozen powder was then collected by sieve filtration and freeze-dried. XRD showed that danazol existed in the substantially amorphous form in the engineered powder. The amorphous nature of danazol in the XRD pattern also verifies that the danazol was included into the HPβCD cavity during equilibration of the solution. The BET specific surface area of the SFL powder (113.50 $m^2/g$) is significantly greater than that of the slowly frozen control (0.17 $m^2/g$), co-ground physical mixture (0.42 $m^2/g$), or bulk danazol (0.52 $m^2/g$). The high surface area of the micronized SFL powder can be attributed to the porous nature of the microparticles that compose the engineered powder. The amount of danazol dissolved from the micronized SFL powder within 2 minutes (100 percent) was significantly greater than that from the slowly frozen control (70 percent) or co-ground physical mixture (20 percent). Measurement of the contact angle of compacts of the various samples investigated allowed for the determination of the wettability of the powders. From Table 6, it can be seen that the micronized SFL powders had significantly lower contact angles (27.0–32.3°) with aqueous dissolution media than did the slowly frozen control (32.0°), the co-ground physical mixture (51.5°) or the danazol alone (64.3°). A lower contact angle coincided with enhanced wettability of the powder in aqueous dissolution media.

TABLE 6

| Determination of contact angle determined against purified water. | |
|---|---|
| Sample | Average Contact Angle ± S.D. |
| SFL Danazol Alone | 64.3 ± 1.1 |
| Co-ground Physical Mixture | 51.5 ± 0.7 |
| Slowly Frozen Control | 32.0 ± 0.0 |
| Micronized SFL Powder | 27.0 ± 2.8 |

Example 5

An aliquot of 2.5 g danazol was dissolved in 372.5 g THF. Aliquots of 1.25 g polyvinyl alcohol (PVA, MW=22,000), 1.25 g polyvinylpyrrolidone (PVP) K-15, and 1.25 g poloxamer 407 were dissolved in purified water. The two solutions were mixed to form a one-phase cosolvent solution. The solution was then processed by SFL and freeze-dried and fluidized in an atmospheric freeze-drying (ATMFD) chamber. The solution was atomized directly into liquid nitrogen through an insulated polyetheretherketone (PEEK) nozzle with a 127 $\mu m$ orifice at 5000 psi constant pressure, which was supplied by an HPLC pump. The atomized frozen powder was then collected by sieve filtration and freeze-dried using a cryogenic atmospheric (ATMFD) fluidized bed apparatus. XRD showed that danazol existed in the substantially amorphous form in micronized SFL powders dried by ATMFD or tray lyophilization. In contrast, crystalline danazol was present in the co-ground physical mixture and slowly frozen control. The specific surface area of the ATMFD micronized SFL powder (5.72 $m^2/g$) is significantly less than that of the tray lyophilized micronized SFL powder (8.90 $m^2/g$), but significantly greater than that of the co-ground physical mixture (1.92 $m^2/g$) or bulk danazol (0.52 $m^2/g$). The microparticles are porous and have a high surface area. The amount of danazol dissolved from the tray lyophilized micronized SFL powder was 93 percent after 2 minutes whereas the amount dissolved from the ATMFD micronized SFL powder was 79 percent within the same time period. By 5 minutes, danazol was completely dissolved from both micronized SFL powders, regardless of the drying technique utilized. The amount of danazol dissolved from the micronized SFL powders was significantly greater than that from the slowly frozen control, co-ground physical mixture or bulk danazol for the first 20 minutes of the dissolution study. Measurement of the contact angle of compacts of the various samples investigated allowed for the determination of the wettability of the powders. From Table 7, it can be seen that the micronized SFL powders had significantly lower contact angles (48.9° for tray lyophilized and 27.5° for ATMFD) with aqueous dissolution media than did the slowly frozen control (55.0°), the co-ground physical mixture (51.5°) or the danazol alone (64.3°). A lower contact angle coincided with a better wettability of the powder in aqueous dissolution media. Thus, the SFL process produced a high surface area, micronized powders containing amorphous danazol dispersed within a polymeric matrix that optimized the aqueous dissolution of an otherwise poorly water soluble API. The ATMFD process is a suitable alternative to tray lyophilization, and ATMFD does not allow for recrystallization of danazol and produces micronized SFL powders with similar dissolution profiles to those dried by tray lyophilization.

TABLE 7

| Investigation of wettability by determination of contact angle against purified water. | |
|---|---|
| Sample | Average Contact Angle ± S.D. |
| SFL Danazol Alone | 64.3 ± 1.1 |
| Co-ground Physical Mixture | 51.5 ± 0.7 |
| Slowly Frozen Control | 55.0 ± 0.42 |
| Tray Lyophilized Micronized SFL Powder | 48.9 ± 2.8 |
| ATMFD Micronized SFL Powder | 27.5 ± 10.5 |

Example 6

An aliquot of 1.0 g danazol was dissolved in 32.33 g ethyl acetate. Aliquots of 0.5 g polyvinyl alcohol (PVA, MW=22,000), 0.5 g polyvinylpyrrolidone (PVP) K-15, and 0.5 g poloxamer 407 were dissolved in purified water. The organic solution was added drop-wise to the aqueous solution as it was being mixed using a rotor/stator type homogenizer. The resulting o/w emulsion was then further processed using a high-pressure homogenizer. The emulsion was then processed by SFL and tray lyophilized. The emulsion was atomized directly into liquid nitrogen through an insulated polyetheretherketone (PEEK) nozzle with a 127 $\mu m$ orifice at 5000 psi constant pressure, which was supplied by an ISCO syringe pump. The atomized frozen powder was then collected by sieve filtration and freeze-dried. XRD showed that the resulting danazol existed in the substantially amorphous form in the micronized SFL powder from emulsion and solution. In contrast, crystalline danazol was present in the co-ground physical mixture. SFL processing of the emulsion produces spherical microparticles about 10–25 μm in diameter. The amount of danazol dissolved from the micronized SFL powder from emulsion was 93 percent after 2 minutes, which is similar to what was dissolved from the SFL powder from solution (93 percent) within the same time period. By 5 minutes, danazol was completely dissolved from both micronized SFL powders, emulsion and solution-based.

Example 7

An aliquot of 100 mg danazol was dissolved in 14.9 g tetrahydrofuran (THF). An aliquot of 200 mg polyoxyethylene-polyoxypropylene copolymer (pluronic F127; poloxamer 407) was dissolved in the 29.8 g purified water. The aqueous and organic solutions were then mixed to obtain danazol/poloxamer 407 (1:2) SFL feed solution. The SFL solution was held in the solution cell. The solution cell was connected to an insulated nozzle which was positioned within the cryogenic liquid when the cryogenic liquid was in the vessel. Liquid nitrogen was used as the cryogenic liquid in this experiment. The nozzle used was polyetheretherketone (PEEK) tubing with a diameter of 63.5 μm. A constant pressure 4000 PSI from the ISCO syringe pump provided a spray flow rate (15 ml/min) for the SFL feed solution. The SFL feed solutions were then sprayed through the nozzle and atomized into small droplets directly into the liquid nitrogen phase. Frozen particles formed instantaneously. The frozen particles were collected and lyophilized by a tray lyophilizer for 48 hrs. The very fine, porous and uniform SFL powder was generated.

XRD indicates that SFL powders containing danazol are substantially amorphous, as compared to highly crystalline bulk danazol.

BET analysis (Table 8) showed that the surface area of the SFL powder was 11.04 m$^2$/g.

This result confirmed the highly porous structure of SFL powders. The contact angle measurement (Table 8) demonstrated that the mean value for SFL danazol/poloxamer 407 powder was 34° against purified water and 25° against FeSSIF.

The SFL danazol powders showed the significantly enhanced dissolution rate. The FeSSIF media used for the danazol dissolution studies reportedly simulate in vivo gastrointestinal fluid; low levels of surfactants were recommended to be included in the dissolution media to give a better correlation between in vitro and in vivo data. The rate of dissolution of micronized bulk danazol was slow; only 21 percent of the danazol dissolved in 60 minutes. The dissolution of the SFL danazol/poloxamer 407 was very fast, the amount dissolved danazol reached 99 percent in only 10 minutes

TABLE 8

The surface area and contact angle of SFL danazol/poloxamer 407 powders investigated.

| Sample | SFL Danazol/Poloxamer 407 |
| --- | --- |
| Surface Area (m$^2$/g) | 11.04 |
| Contact Angle Degrees (Purified Water) | 34 |
| Contact Angle Degrees (FeSSIF) | 25 |

Example 8

CBZ and SLS were dissolved in a THF/water co-solvent system, and then processed using the SFL technology. The SFL feed solution was placed into the solution cell. A constant pressure 4000 PSI from the ISCO syringe pump provided a spray flow rate for the SFL feed solution. The SFL feed solutions were then sprayed through a 63.5 μm diameter PEEK nozzle and atomized into small droplets directly into the liquid nitrogen phase. Frozen particles formed instantaneously. The frozen particles were collected and lyophilized.

The very fine, porous and uniform SFL CBZ/SLS powders were generated. The ratio of CBZ and SLS in the SFL powder is one to one. The particle size distribution for the SFL powders and bulk micronized CBZ (Table 9) were determined in an AERO-DISPERSER based on a time-of-flight measurements. The mean particle diameter of the SFL CBZ/SLS powders was 7.11 μm, which is significantly decreased compared to 39.70 μm of the CBZ starting materials. The span index is used to described the polydispersity in a given particle size distribution and is defined as (D90-D10)/D50, where D10, D50, and D90 are the respective particle size at 10, 50, 90 percent cumulative percent undersize. The span index of SFL CBZ/SLS was 1.31 indicating polydispersity. The contact angle measurement (Table 10) demonstrated that the mean value for the SFL CBZ/SLS powders was 24° against the purified water. BET analysis (Table 10) showed that the surface area of the SFL CBZ/SLS powders was 12.81 m$^2$/g. The dissolved CBZ from the SFL CBZ/SLS powders was 94 percent in only 5 minutes.

TABLE 9

The particle size distribution of SFL CBZ/SLS powders and bulk micronized CBZ.

| | SFL CBZ/SLS | Bulk CBZ |
| --- | --- | --- |
| D10 (μm) | 1.33 | 15.56 |
| D50 (μm) | 7.11 | 39.70 |
| D90 (μm) | 10.61 | 132.33 |
| Span Index | 1.31 | 2.94 |

TABLE 10

The surface area and contact angle of CBZ powders.

| Sample | SFL CBZ/SLS Powders |
| --- | --- |
| Surface Area (m$^2$/g) | 12.81 |
| Contact Angle Degrees (Purified Water) | 24 |

Example 9

SFL CBZ/PVP K15/poloxamer 407 powders were prepared according to the following procedure. The SFL feed solution was prepared by dissolving 200 mg CBZ and 100 mg poloxamer 407 and 100 mg PVP K-15 in the acetonitrile solvent. The SFL feed solution was then placed into the solution cell. A constant pressure 2000 PSI from the ISCO syringe pump provided a spray flow rate for the SFL feed solution. The SFL feed solutions were then sprayed through a 63.5 μm diameter PEEK nozzle and atomized into small droplets directly into the liquid nitrogen phase. Frozen particles formed instantaneously. The frozen particles were collected and vacuum dried 12 hours. The very fine, porous and uniform SFL CBZ/PVP K-15/poloxamer 407 powders were generated. The ratio of CBZ and excipients in the SFL powder was one to one. Powder XRD analysis indicated the substantially amorphous nature of CBZ. Significant improvements in the dissolution rates were found for SFL CBZ/ PVP K-15/poloxamer 407 powders. The amount of CBZ dissolved CBZ from SFL CBZ/PVP K-15/poloxamer 407 powders was 95 percent within 5 minutes.

Example 10

SFL TAA/PVP K-15/poloxamer 407 powder was generated. The ratio of TAA and excipients in the SFL powder is 1:1. Powder XRD analysis indicated that the TAA was substantially amorphous. 90 percent of the TAA was dissolved at 10 minutes for the SFL powder.

Although the invention has been described in connection with specific embodiments, it should be understood that the invention as claimed should not be unduly limited to such specific embodiments. Modifications and variations of the described compositions and methods of the invention will be apparent to those skilled in the art without departing from the scope and spirit of the invention. Indeed, various modifications of the described compositions and modes of carrying out the invention which are obvious to those skilled in the art or related arts are intended to be within the scope of the following claims.

What is claimed is:

1. A system for preparing particles comprising:
   a solution source comprising an effective ingredient;
   a vessel containing a cryogenic liquid selected from the group consisting of carbon dioxide, nitrogen, ethane, propane, helium, argon, or isopentane; and
   an insulating nozzle having an end and a tip, wherein the end of the insulating nozzle is connected to the solution source and the tip is placed at or below the level of the cryogenic liquid.

2. The system recited in claim 1, wherein the effective ingredient is a pharmaceutical.

3. The system recited in claim 2, wherein the effective ingredient is chosen from the group consisting of proteins, peptides, albuterol sulfate, terbutaline sulfate, diphenhydramine hydrochloride, chlorpheniramine maleate, loratidine hydrochloride, fexofenadine hydrochloride, phenylbutazone, nifedipine, carbamazepine, naproxen, cyclosporin, betamethosone, danazol, dexamethasone, prednisone, hydrocortisone, 17 beta-estradiol, ketoconazole, mefenamic acid, beclomethasone, alprazolam, midazolam, miconazole, ibuprofen, ketoprofen, prednisolone, methylprednisone, phenytoin, testosterone, flunisolide, diflunisal, budesonide, fluticasone; insulin, glucagon-like peptide, C-Peptide, erythropoietin, calcitonin, human growth hormone, leutenizing hormone, prolactin, adrenocorticotropic hormone, leuprolide, interferon alpha-2b, interferon beta-1a, sargramostim, aldesleukin, interferon alpha-2a, interferon alpha-n3alpha,-proteinase inhibitor; etidronate, nafarelin, chorionic gonadotropin, prostaglandin E2, epoprostenol, acarbose, metformin, or desmopressin, cyclodextrin, antibiotics; and the pharmacologically acceptable organic and inorganic salts or metal complex thereof.

4. The system recited in claim 1, wherein the solution source further comprises water, at least one organic solvent, or a combination thereof.

5. The system recited in claim 4, wherein the organic solvent is selected from the group consisting of water miscible solvents and non-water miscibl solvents.

6. The system recited in claim 5, wherein the organic solvent is elected from the group consisting of ethanol, methanol, tetrahydrofuran, acetonitril acetone, tert-butyl alcohol, dimethyl sulfoxide, N,N-dimethyl formamide, diethyl ether, methylene chloride, ethyl acetate, isopropyl acetate, butyl acetate, propyl acetate, toluene, hexanes, heptane, pentane, and combinations thereof.

7. The system recited in claim 1, wherein the solution source further comprises an excipient, an adjuvant, an absorption enhancer, a release-rate controlling polymer, a stability enhancer, or combinations thereof.

8. The system recited in claim 1, wherein the tip of the insulating nozzle has a diameter of between 1 micron and 1 centimeter.

9. A method for spray freezing comprising:
   mixing an effective ingredient with a solution agent;
   spraying the effective ingredient-solution agent mixture through an insulating nozzle located at or below the level of a cryogenic liquid, wherein the spray rapidly generates frozen particles having a size range of 10nm to 10 microns.

10. The method recited in claim 9, wherein the solution agent is selected from water, at least one organic solvent, or a combination thereof.

11. The method recited in claim 9, further comprising collecting the frozen particles.

12. The method recited in claim 9, wherein the effective ingredient is a water soluble pharmaceutical or a poorly water soluble pharmaceutical.

13. The method recited in claim 9, further comprising drying the frozen particles to substantially remove the water.

14. The method recited in claim 13, wherein the frozen particles are dried in a fluidized bed with a gas cooled to below the melting point of the frozen particles.

* * * * *